United States Patent
Iwasaka et al.

(10) Patent No.: US 10,028,642 B2
(45) Date of Patent: Jul. 24, 2018

(54) ENDOSCOPE

(71) Applicant: FUJIFILM Corporation, Tokyo (JP)

(72) Inventors: Masayuki Iwasaka, Kanagawa (JP);
Teruyuki Emura, Kanagawa (JP);
Sunao Hachisuka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

(21) Appl. No.: 15/073,654

(22) Filed: Mar. 18, 2016

(65) Prior Publication Data
US 2016/0270633 A1 Sep. 22, 2016

(30) Foreign Application Priority Data
Mar. 20, 2015 (JP) .................. 2015-058348

(51) Int. Cl.
*A61B 1/00* (2006.01)

(52) U.S. Cl.
CPC ......... *A61B 1/00098* (2013.01); *A61B 1/0011* (2013.01); *A61B 1/00137* (2013.01)

(58) Field of Classification Search
CPC ........................ A61B 1/00098; A61B 1/00101
USPC ................. 600/106, 107, 127, 133
See application file for complete search history.

(56) References Cited

U.S. PATENT DOCUMENTS

| 5,562,600 A | * | 10/1996 | Matsuno | A61B 1/018 600/107 |
| 5,569,157 A | * | 10/1996 | Nakazawa | A61B 1/0008 600/104 |
| 5,730,701 A | * | 3/1998 | Furukawa | A61B 1/0008 600/121 |
| 8,246,534 B2 | * | 8/2012 | Yamaya | A61B 1/00098 600/104 |
| 2004/0082836 A1 | | 4/2004 | Hino | |
| 2007/0270638 A1 | * | 11/2007 | Kitano | A61B 1/00098 600/104 |

FOREIGN PATENT DOCUMENTS

JP 2004-141315 5/2004

\* cited by examiner

*Primary Examiner* — Alexandra L Newton
*Assistant Examiner* — Rynae Boler
(74) *Attorney, Agent, or Firm* — JCIPRNET

(57) ABSTRACT

There is provided an endoscope which can clean a distal end portion promptly and easily. An elevator housed in an elevator housing space of a distal end portion body is coupled with an erecting lever of an erecting lever housing chamber through a rotating shaft. A rotating shaft receiving portion formed with an engagement hole engaged with the rotating shaft and an engagement hole loosely fitted thereto is provided in the elevator, the elevator is retreated from the elevator housing slit by loosely fitting the elevator to the rotating shaft in cleaning.

10 Claims, 13 Drawing Sheets

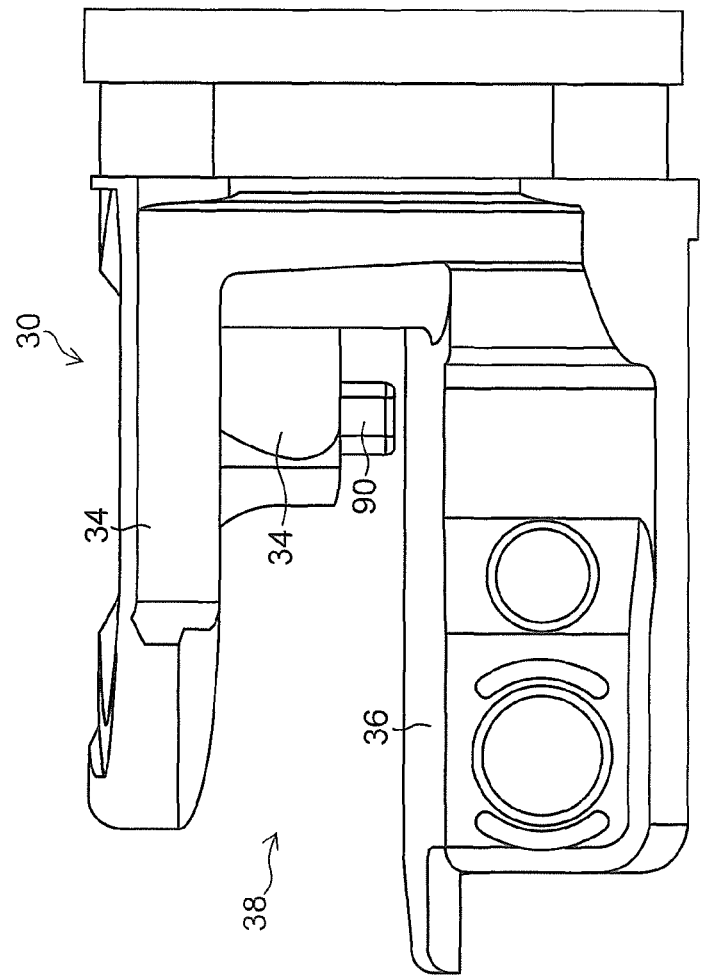

ENDOSCOPE

CROSS-REFERENCE TO RELATED APPLICATIONS

The present application claims priority under 35 U.S.C. § 119 to Japanese Patent Application No. 2015-058348, filed on Mar. 20, 2015. Each of the above application(s) is hereby expressly incorporated by reference, in their entirety, into the present application.

BACKGROUND OF THE INVENTION

Field of the Invention

The present invention relates to an endoscope, and specifically relates to an endoscope including an elevator.

Description of the Related Art

Regarding an endoscope, various treatment tools are inserted into a treatment-tool entry port provided on an operation portion and they are led out of the treatment-tool exit port opened in the distal end portion and used for treatment. The treatment tools such as a guide wire, a contrast medium tube and the like are used for a duodenoscopy, puncture needles for an ultrasonic endoscope, and forceps, snares and the like for a direct-viewing endoscope or a side-viewing endoscope, for example. These treatment tools need to change a derivation direction at the distal end portion in order to treat a desired position in a subject, and thus, a treatment-tool elevating mechanism (forceps elevator, hereinafter referred to as an "elevator") is provided on the distal end portion.

As such the treatment-tool elevating mechanisms, a mechanism in which a wire is attached to the elevator and extended to a proximal end side of the endoscope, is known. In the mechanism, the elevator is rotated around a rotating shaft by pushing and pulling operation of the wire with an operation lever provided on the operation portion so as to change a position of the elevator between an erecting position and a reclining position. Moreover, a mechanism (lever type) in which the rotating shaft of the elevator is coupled with a housed lever through a partition wall, and the wire is attached to the lever is also known. In the mechanism, the elevator is rotated around the rotating shaft by means of the pushing and pulling operation of the wire with the operation lever provided on the operation portion so as to change the position of the elevator between the erecting position and the reclining position.

The distal end portion provided with such a treatment-tool elevating mechanism has a complicated shape and structure and thus, improvement of cleaning performances such as wraparound of a disinfectant, insertion of a cleaning brush (reachability of a tip end of the brush) or drainage and ease of a cleaning work are in demand. Conventionally, an endoscope having a detachable cap on the distal end portion is known (see Japanese Patent Laid-Open No. 2004-141315, for example). In this type of endoscope, the cap is removed after treatment, and then the distal end portion is cleaned.

SUMMARY OF THE INVENTION

However, in an endoscope in the related art as described in Japanese Patent Laid-Open No. 2004-141315, in addition to the fact that a distal end portion itself is originally small, exposed portions are small because an elevator is housed in an elevator housing slit. Moreover, the gap between the elevator and the elevator housing slit is narrow, and therefore it takes time for cleaning using a brush or the like.

The present invention has been made in view of such circumstances, and it is an object to provide an endoscope which can clean a distal end portion promptly and easily.

To attain the above-mentioned object, an endoscope according to one aspect of the present invention including: an insertion portion which includes a distal end and a proximal end; an operation portion which is provided on a proximal end side of the insertion portion and includes an operating member and; a distal end portion body which is provided on a distal end side of the insertion portion, and has a front surface being a surface in a longitudinal direction of the insertion portion, an upper surface being a surface in a direction in which a treatment tool is led out with respect to the longitudinal direction and a lower surface being a surface on a side opposite to the upper surface with respect to the longitudinal direction; an elevator which is rotatably provided in the distal end portion body; a rotating shaft provided with an axis and configured to rotate the elevator around the axis, wherein a cross section vertical to a direction of the axis has a non-circular shape; a rotating shaft receiving portion provided in the elevator, the rotating shaft receiving portion including a first rotating shaft receiving region which is engaged with the rotating shaft in a relatively unrotatable manner and a second rotating shaft receiving region which is loosely fitted to the rotating shaft in a relatively rotatable manner; an elevator erecting mechanism configured to rotate the rotating shaft; an operating wire which includes a proximal-end-side coupling portion coupled with the operating member and a distal-end-side coupling portion coupled with the elevator erecting mechanism, the operating wire being configured to rotate the rotating shaft to recline or erect the elevator by being pushed or pulled by an operation of the operating member; an elevator housing slit which is provided in the distal end portion body and forms a space portion to house the elevator, the elevator housing slit including an opening on a side of the upper surface, on a side of the lower surface and on a side of the front surface; and a cap which is detachably provided in the distal end portion body, the cap including an opening window which opens a part of the opening on the side of the upper surface and a partition wall portion which closes a part of the opening on the side of the lower surface in a state in which the cap is attached to the distal end portion body, wherein, the distal end portion body includes a position restricting portion which is configured to restrict a position of a rotating shaft receiving region of the rotating shaft receiving portion with respect to the rotating shaft; and when the elevator is located in a first position in a rotation direction, the position restricting portion restricts the position of the rotating shaft receiving region of the rotating shaft receiving portion with respect to the rotating shaft to the first rotating shaft receiving region, and, when the elevator is located in a second position in the rotation direction, the position restricting portion allows the position of the rotating shaft receiving region of the rotating shaft receiving portion with respect to the rotating shaft to move from the first rotating shaft receiving region to the second rotating shaft receiving region.

According to the aspect, since it is possible to retreat most of the elevator to the outside of the elevator housing slit and clean the elevator and the elevator housing slit, it is possible to perform cleaning easily and promptly.

In an endoscope according to another aspect of the present invention, the first position is a position in which a whole of the elevator is housed inside the elevator housing slit.

In the endoscope according to another aspect of the present invention, the second position is a position in which at least part of the elevator is exposed to the outside of the elevator housing slit.

In an endoscope according to another aspect of the present invention, the second position is a position in which at least a part of the elevator is exposed from the part of the opening on the side of the lower surface to the outside.

In an endoscope according to another aspect of the present invention, the second position is a position in which at least a part of the elevator is exposed from the part of the opening on the side of the upper surface to the outside.

In an endoscope according to another aspect of the present invention, the rotating shaft is configured in a cantilever shape in which one end of the rotating shaft is a fixed end fixed to the elevator erecting mechanism and another end is a free end.

In an endoscope according to another aspect of the present invention, the elevator erecting mechanism includes an elevator erecting lever coupled with the rotating shaft; the distal-end-side coupling portion of the operating wire is coupled with the elevator erecting lever; and, when the operating wire is pushed or pulled by operation of the operating member, the operating wire rotates the rotating shaft through the elevator erecting lever to recline or erect the elevator.

According to the present invention, it is possible to clean a distal end portion promptly and easily.

BRIEF DESCRIPTION OF THE DRAWINGS

FIG. 9 is a plan view illustrating the distal end portion body from the upper side;

DETAILED DESCRIPTION OF THE EMBODIMENTS

In the following, preferable embodiments of the present invention are described in detail with reference to the accompanying drawings.

Figure 1:
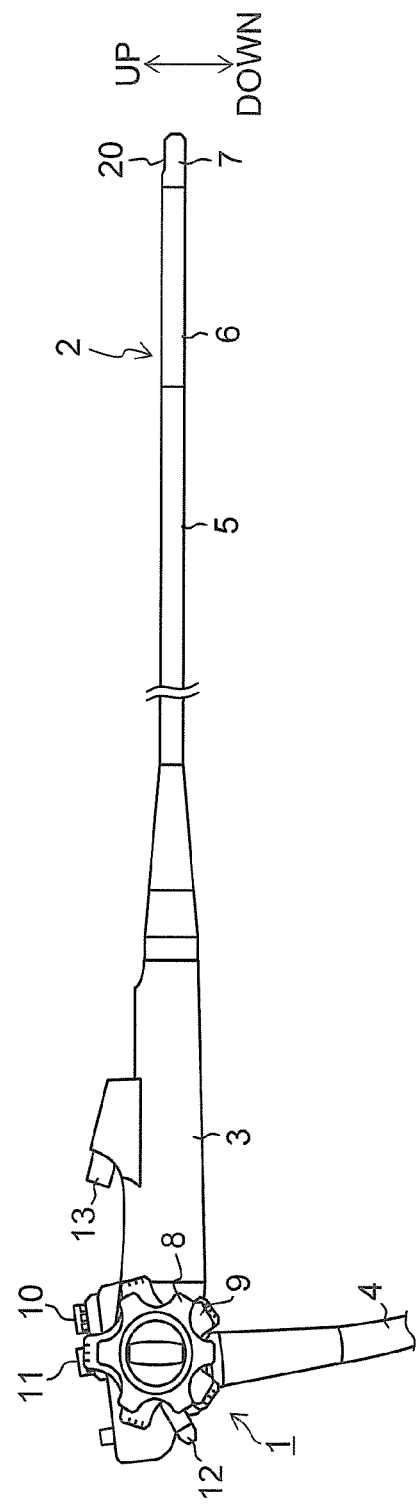
FIG. 1 is a configuration diagram illustrating an endoscope 1 according to the present invention.

FIG. 1 is a configuration diagram illustrating the endoscope 1 according to the present invention.

The endoscope 1 in this figure includes an insertion portion 2 which is to be inserted in a patient's body, an operation portion 3 which is continuously provided in the proximal end surface of the insertion portion 2 and is used to hold the endoscope 1 and operate the insertion portion 2, and a universal cord 4 which connects the endoscope 1 with system configuration equipment such as an unillustrated light source device and processor device, and so on.

The insertion portion 2 is formed with a flexible portion 5, a bending portion 6 and a distal end portion 7 which are provided in this order from the proximal end to the distal end. The flexible portion 5 has flexibility and bends in an arbitrary direction along an insertion path of the insertion portion 2. The bending portion 6 bends in each of the upper, lower, right and left directions by operation of each of angle knobs 8 and 9 of the operation portion 3. The distal end portion 7 includes an observing portion that takes an image of an observed site in a body and sends the taken image to a processor device connected by the universal cord 4 as an observation image (endoscope image), and an illuminating portion that emits illumination light, which is propagated from a light source device connected by the universal cord 4 through a light guide inside the endoscope 1, to the observed site, and so on.

Figure 2:
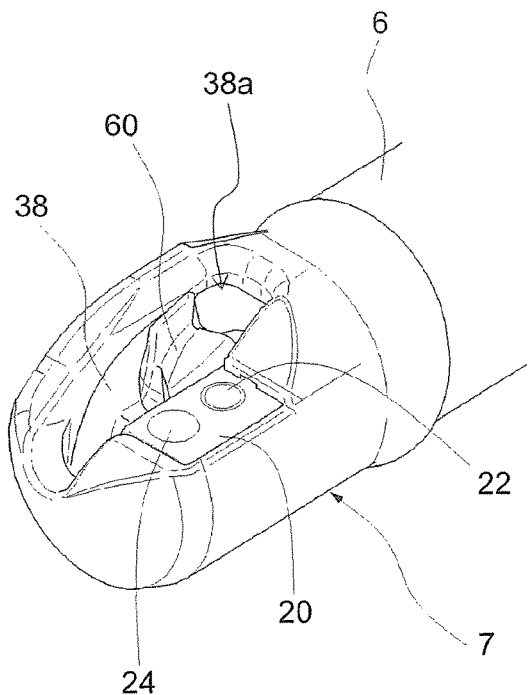
FIG. 2 is an expanded perspective view that illustrates a distal end portion.

FIG. 2 is an expanded perspective view that illustrates the distal end portion 7. The endoscope 1 of the present embodiment is a side-viewing endoscope used as a duodenoscope, for example, and the distal end portion 7 in this figure shows a configuration in the side-viewing endoscope.

As illustrated in the figure, a flat surface 20 which is substantially parallel to a longitudinal axis that is the axis of the insertion portion 2 is provided in the distal end portion 7, and the observation window 22 and an illumination window 24 are provided in the flat surface 20. Here, in the following, in a case where the longitudinal axis is merely referred to, the longitudinal axis of the insertion portion 2 is shown.

The observation window 22 is a component of the observing portion which obtains an image of an observed site that exists on the lateral side (radial direction) with respect to the longitudinal axis, and receives object light from an observed portion on the lateral side in an optical system (an imaging lens or the like) and an imaging device that are other components of the observing portion. The illumination window 24 is a component of the illuminating portion mounted to the distal end portion 7, and emits illumination light to the observed site from a light emitting portion which is another component of the illuminating portion, that is, from the light emitting portion provided in a termination portion of the light guide which propagates light from a light source device.

Here, as for the distal end portion 7, a position on the distal end side which is a longitudinal axis direction is the front side (distal end side), a position on the opposite side thereof is the rear side (proximal end side), a position which is in a direction vertical to the flat surface 20 and is opposed to the flat surface 20 is the upper side, the opposite side thereof is the lower side (see FIG. 1), and the left side and the right side are positions in a direction decided by the relationship between the front and rear position and the upper and lower position.

Moreover, an elevator housing slit 38 is provided on the right side of the flat surface 20 in the distal end portion 7, and an elevator 60 is provided in the elevator housing slit 38. The elevator housing slit 38 communicates with a treatment tool introduction port 13 (see FIG. 1) of the operation portion 3 through a treatment tool insertion channel inserted in the insertion portion 2, and a treatment tool inserted from the treatment tool introduction port 13 is led to the elevator housing slit 38.

The elevator 60 bends the travelling direction of the treatment tool led to the elevator housing slit 38, guides it to a direction toward the opening portion (opening) 38a (which may be referred to as a "treatment entry port 38a") on the upper surface side of the elevator housing slit 38, and leads out the treatment tool from the treatment entry port 38a.

Moreover, the elevator 60 performs erecting and reclining operation (rotates) in a direction for erecting (erecting direction) or a direction for falling (falling direction) by operation of an erecting operation lever 12 (see FIG. 1) of the operation portion 3, and changes the delivery direction (delivery angle) of the treatment tool from the treatment entry port 38a.

Here, an unillustrated air-supply and water-supply nozzle which can switch between air supply and water supply to the observation window 22 by operation of an air-supply and water-supply button 10 (see FIG. 1) of the operation portion 3 is provided near the observation window 22 of the flat surface 20. Moreover, a suction channel is connected with the treatment tool insertion channel in the insertion portion 2, and suction from the elevator housing slit 38 is performed by operation of a suction button 11 of the operation portion 3 (see FIG. 1).

Subsequently, a configuration related to the drive mechanism of the elevator 60 in the distal end portion 7 is described in detail.

Figure 3:
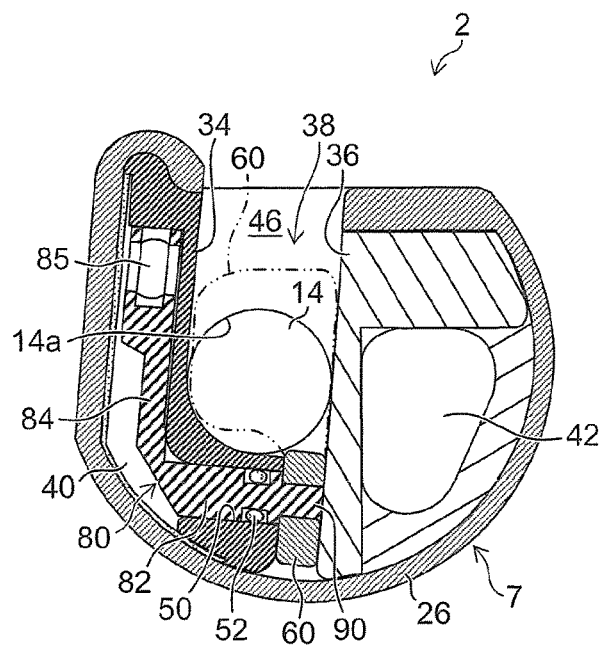
FIG. 3 is a cross-sectional view of the distal end portion.
Figure 4:
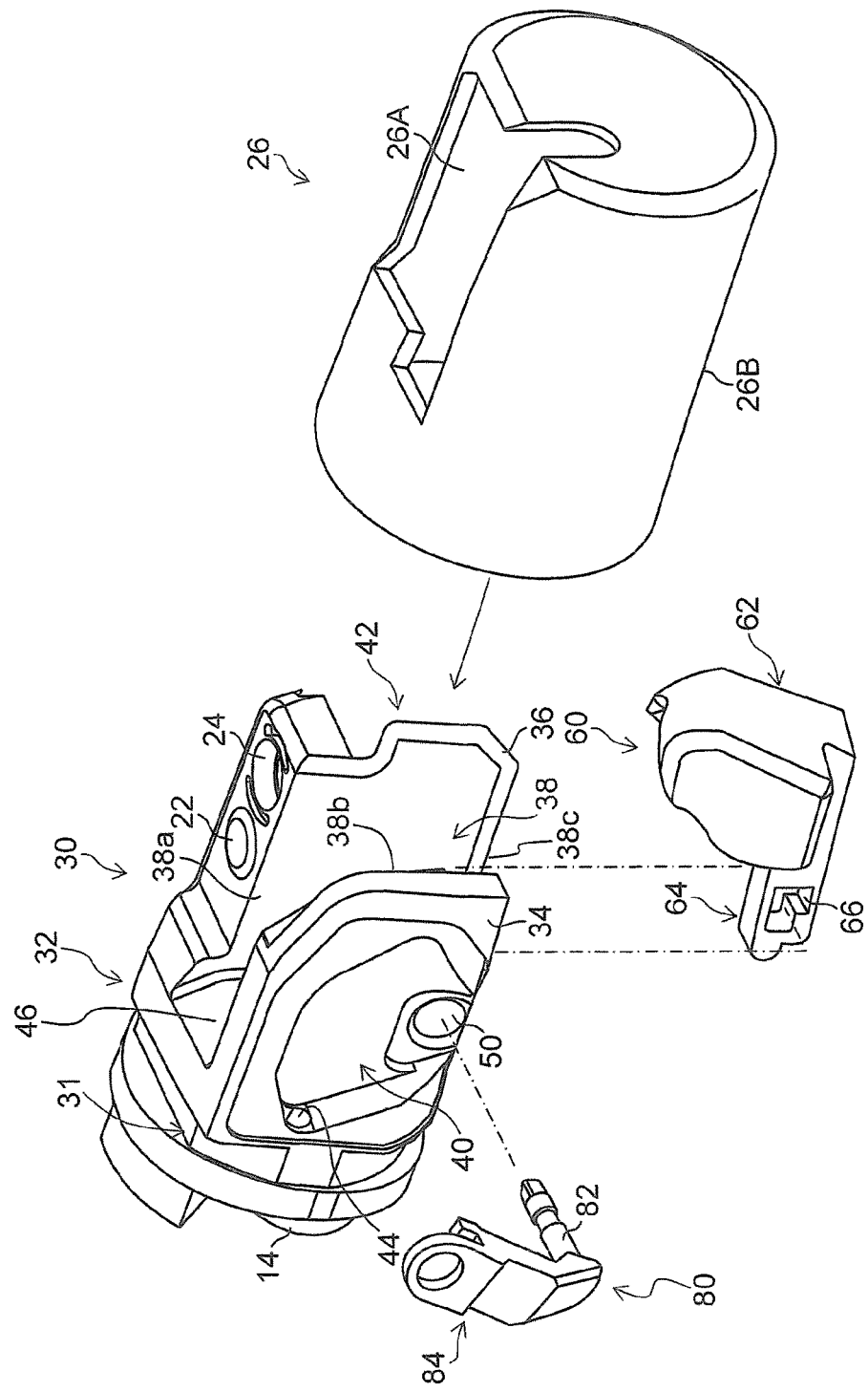
FIG. 4 is an exploded perspective view of a distal end portion.

FIG. 3 is a cross-sectional view of the distal end portion 7 vertical to the longitudinal axis, and FIG. 4 is an exploded perspective view of the distal end portion 7.

As illustrated in these figures, the distal end portion 7 includes a distal end portion body 30 (see FIG. 4) which divides the inside of the distal end portion 7 into a plurality of regions and to which various components are integrally assembled, and is covered with a cap 26 which is detachable for the outer peripheral portion of the distal end portion body 30.

The cap 26 is made of an elastic material such as elastic rubber and formed in a shape based on a cylindrical shape in which the distal end side is closed, and includes: an opening window 26A which opens the above-mentioned flat surface 20, the whole of the opening portion 38a (treatment entry port 38a) on the upper surface side of the elevator housing slit 38 and a part on the upper side of an opening portion 38b on the front surface side; and a partition wall portion 26B which closes the whole of an opening portion 38c on the lower surface side of the elevator housing slit 38 and a part on the lower side of the opening portion 38b on the front surface side.

Moreover, an engagement portion (not illustrated) which annularly projects toward the inside in the radial direction is formed in the proximal end of the cap 26, and the cap 26 is attached to the distal end portion body 30 by engaging the engagement portion with a groove 31 formed in the outer peripheral portion of the distal end portion body 30. Moreover, the cap 26 is detached at the time of cleaning as described later.

The distal end portion body 30 is formed with a rigid member such as a metal material having corrosion resistance, and includes a columnar proximal end portion 32 on the proximal end side and a pair of right and left side wall portions 34 and 36 which are extended from the proximal end portion 32 to the distal end side and face each other. By this means, in the distal end portion 7, the elevator housing slit 38 that is a space portion which houses the elevator 60 is formed between the right side wall portion 34 and the left side wall portion 36, an erecting lever housing chamber 40 that is a space portion which houses an erecting lever 84 described below is formed on the right side from the side wall portion 34, and an optical system housing chamber 42 that is a space portion which houses components (not illustrated) of the above-mentioned observing portion and illuminating portion is formed on the left side from the side wall portion 36. Here, the erecting lever housing chamber 40 and the optical system housing chamber 42 are covered with an unillustrated protective plate in FIG. 4 to hold airtightness.

In a state in which the cap 26 is detached from the distal end portion body 30 as illustrated in FIG. 4, the elevator housing slit 38 includes an opening portion on the upper surface side as the opening portion 38a (treatment entry port 38a), an opening portion on the front surface side as the opening portion 38b and an opening portion on the lower surface side as the opening portion 38c. And the elevator housing slit 38 extends and opens from the upper surface to the lower surface through the front surface since those opening portions 38a, 38b and 38c are continuously provided.

Moreover, a rear wall portion 46 formed with the proximal end portion 32 of the distal end portion body 30 is disposed on the proximal end side of the elevator housing slit 38, and an opening portion 14a that is a conduit end portion of a treatment tool insertion channel 14 is disposed in the rear wall portion 46 as illustrated in FIG. 3.

The elevator 60 whose entire image is illustrated in FIG. 4 is rotatably installed in this elevator housing slit 38. Here, the configuration of the elevator 60 is described later.

A holding hole 50 that penetrates from the erecting lever housing chamber 40 to the elevator housing slit 38 as illustrated in FIGS. 3 and 4 is formed near the lower end of the side wall portion 34 disposed on the right side of the elevator housing slit 38, and a rotating shaft 82 is rotatably supported to the holding hole 50.

Here, in the present embodiment, as illustrated in FIG. 4, the rotating shaft 82 is integrally formed with the erecting lever 84, is extended from the proximal end of the erecting lever 84 that extends in a tabular shape, and is formed in a cantilever shape such that one end of the rotating shaft 82 is a fixed end which is fixed to the erecting lever 84 that is an elevator erecting mechanism and the other end is a free end. A member including this rotating shaft 82 and the erecting lever 84 that extends in a direction substantially vertical to the axis of the rotating shaft 82 is a driving member 80, but the rotating shaft 82 and the erecting lever 84 may be formed separately from each other.

Moreover, a seal member 52 is disposed between the rotating shaft 82 and the holding hole 50 as illustrated in FIG. 3, and the gas and the liquid are prevented from mutually entering between the elevator housing slit 38 and the erecting lever housing chamber 40.

An end portion (engaging convex portion 90) which projects to an elevator housing slit 38 of this rotating shaft 82 is coupled with an elevator 60 as described later.

As illustrated in FIG. 4, a fan-shaped space portion centering on the holding hole 50 is formed on the right side of the side wall portion 34 as the erecting lever housing chamber 40. In this erecting lever housing chamber 40, the rotating shaft 82 of the driving member 80 is inserted in the holding hole 50 and the erecting lever 84 of the driving member 80 is housed.

Figure 5:
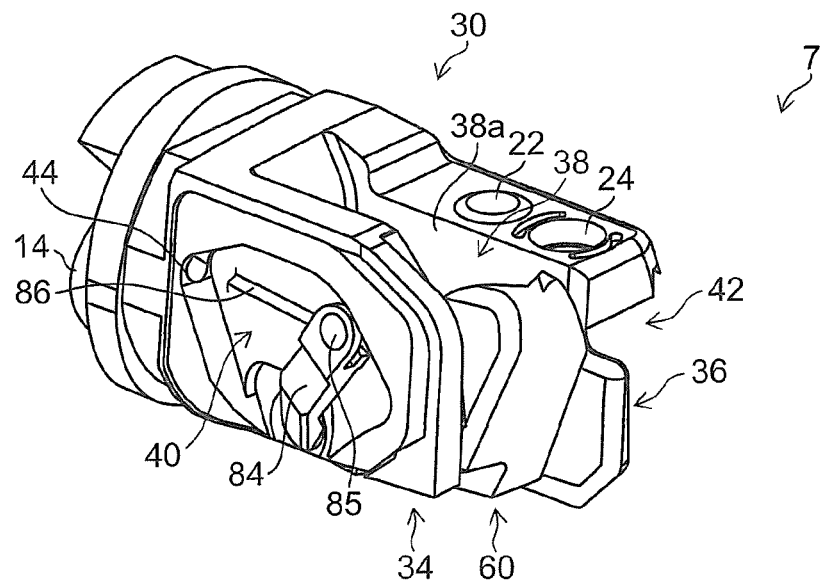
FIG. 5 is a perspective view illustrating a state in which an elevator and a driving member are assembled to a distal end portion body.

FIG. 5 is a perspective view illustrating a state in which the elevator 60 and the driving member 80 are assembled to the distal end portion body 30. Here, a protective plate that covers the erecting lever housing chamber 40 is omitted.

As illustrated in the figure, the distal end portion of an operating wire 86 is coupled with the distal end of the erecting lever 84 through a coupling tool 85. The operating wire 86 is inserted in the insertion portion 2 from a wire insertion hole 44 opened to the wall surface of the erecting lever housing chamber 40 and is coupled with the erecting operation lever 12 of the operation portion 3.

By this means, the operating wire 86 is pushed or pulled by operation of the erecting operation lever 12, and the erecting lever 84 rotates together with the rotating shaft 82. Further, the elevator 60 rotates by the rotation of the rotating shaft 82, and the elevator 60 performs erecting and reclining operation. Here, an elevator erecting mechanism that rotates the rotating shaft 82 is not limited to the one of the present embodiment which pushes or pulls the erecting lever 84 by the operating wire 86.

Next, a coupling mechanism between the elevator 60 and the rotating shaft 82, and so on, are described.

Figure 6:
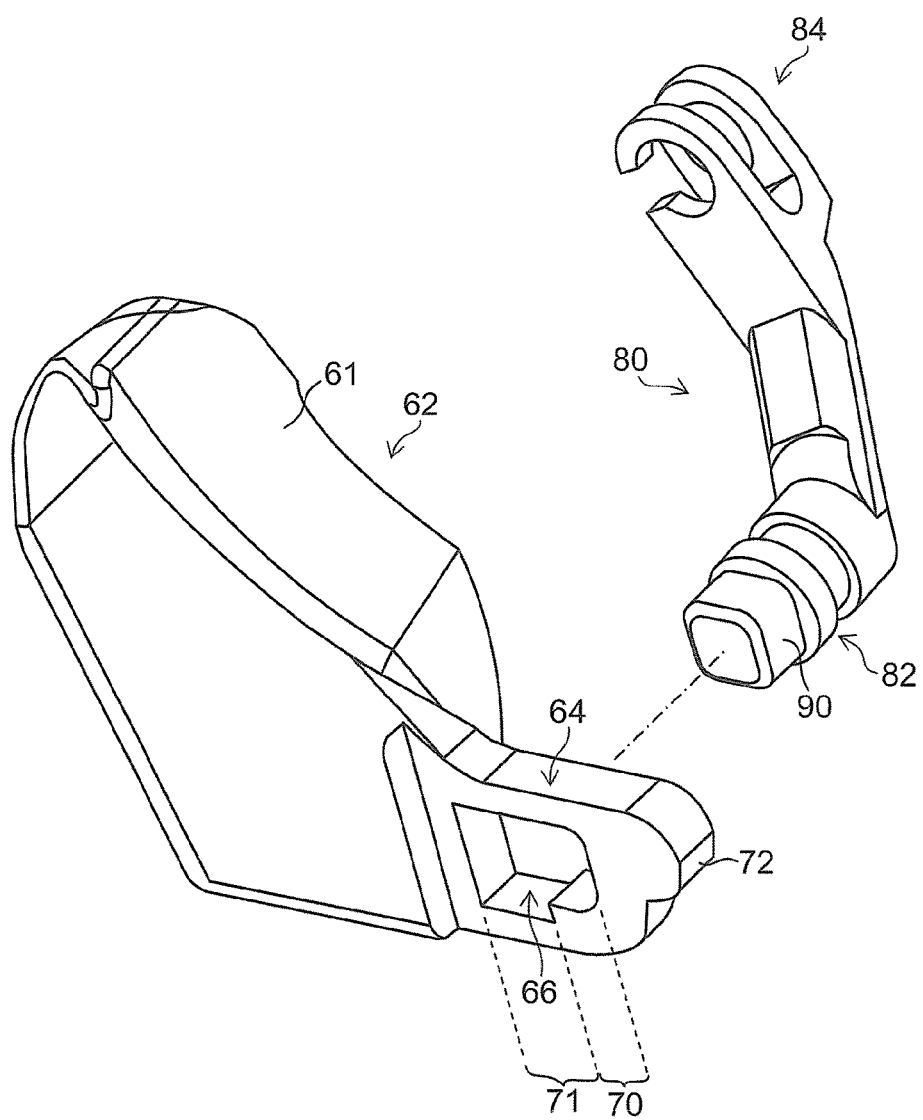
FIG. 6 is a perspective view illustrating an elevator and a driving member.

FIG. 6 is a perspective view illustrating only the elevator 60 and the driving member 80.

As illustrated in FIG. 6 and FIG. 4, the engaging convex portion 90 whose cross-sectional surface vertical to the shaft direction is substantially square as one mode of a non-circular shape is projected in the distal end of the rotating shaft 82 of the driving member 80

As illustrated in FIG. 3, only a portion of the engaging convex portion 90 projects from the holding hole 50 of the side wall portion 34 to the elevator housing slit 38, and the distal end thereof is disposed near the side wall portion 36.

Here, FIG. 9 is a plan view illustrating the distal end portion body 30 from the upper side, in which illustration of the elevator 60 is omitted. As understood from this figure and FIG. 3, a portion in which the holding hole 50 of the side wall portion 34 is formed projects in a direction approaching the side wall portion 36 so as to narrow a gap between the side wall portion 36 and the side wall portion 34. Therefore, the distal end of the engaging convex portion 90 of the rotating shaft 82 and the side wall portion 36 are disposed closely to each other.

Meanwhile, the elevator 60 includes: an elevator body 62 having a guide surface 61 which guides a treatment tool led out from the opening portion 14a of the treatment tool insertion channel 14 to the direction of the treatment entry port 38a; and a coupling portion 64 which projects to the proximal end side from the elevator body 62 and is formed with a narrower width than the elevator body 62.

A rotating shaft receiving portion 66 formed with a hole in which the engaging convex portion 90 of the rotating shaft 82 is inserted is provided in the coupling portion 64. The rotating shaft receiving portion 66 includes a first rotating shaft receiving region 70 engaged with the engaging convex portion 90 of the rotating shaft 82 in a relatively unrotatable manner and a second rotating shaft receiving region 71 loosely fitted to the engaging convex portion 90 of the rotating shaft 82 in a relativity rotatable manner.

Figure 7:
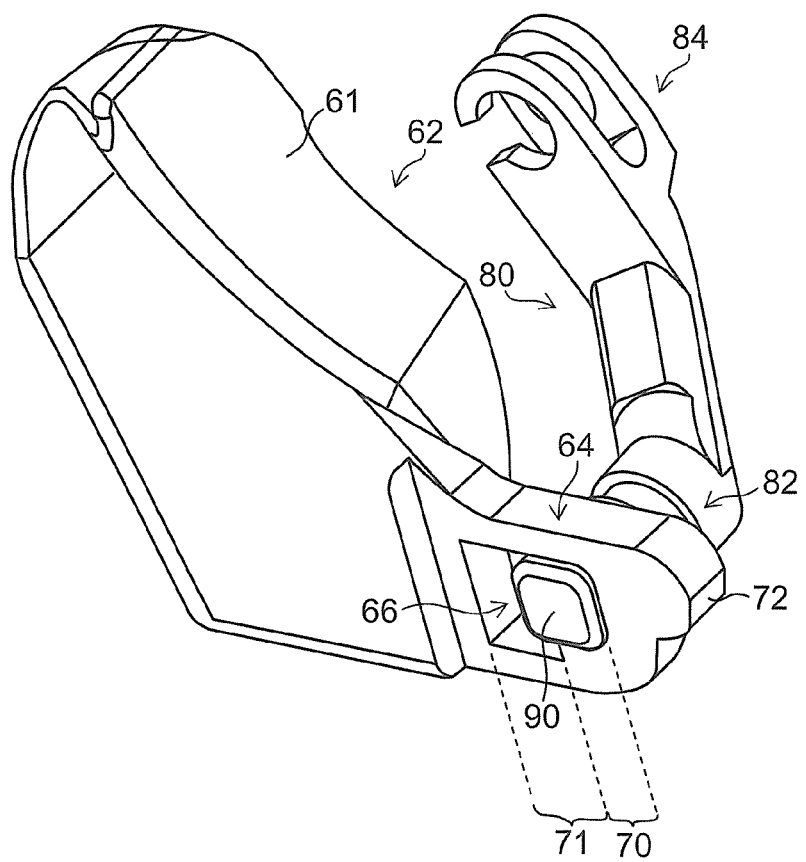
FIG. 7 is a perspective view illustrating the elevator and the driving member.

That is, the first rotating shaft receiving region 70 is an engagement hole which substantially agrees with the shape and size of the engaging convex portion 90 of the rotating shaft 82, and, when this first rotating shaft receiving region 70 is engaged with the engaging convex portion 90 of the rotating shaft 82 as illustrated in FIG. 7, the rotating shaft 82 and the elevator 60 are coupled in a state where they synchronously rotate.

When the endoscope 1 is normally used for operation, it is set to this state.

Figure 8:
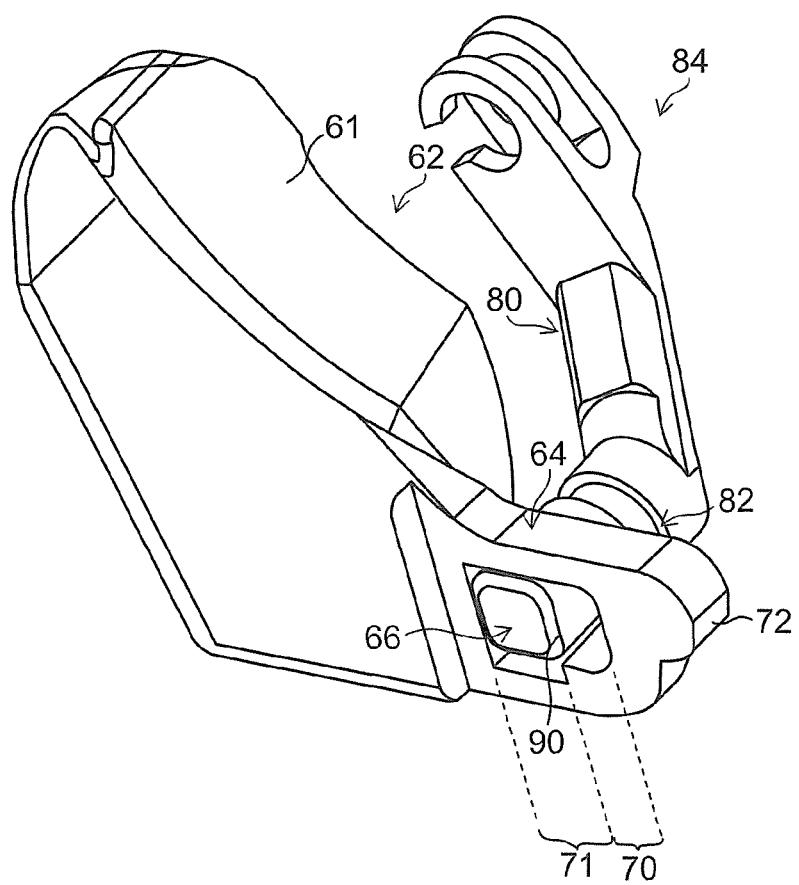
FIG. 8 is a perspective view illustrating the elevator and the driving member.

Meanwhile, the second rotating shaft receiving region 71 is a larger hole than the engaging convex portion 90 of the rotating shaft 82. When the elevator 60 moves toward the proximal end side and the second rotating shaft receiving region 71 moves to the position of the first rotating shaft receiving region 70, the hole of the second rotating shaft receiving region 71 is loosely fitted to the engaging convex portion 90 of the rotating shaft 82 as illustrated in FIG. 8. Therefore, the coupling between the rotating shaft 82 and the elevator 60 is released. At this time, by directly applying a force to the elevator 60, the elevator enters a state in which only the elevator 60 can be rotated around the axis of the rotating shaft 82 without the rotation of the erecting lever 84 and the rotating shaft 82.

By setting the elevator 60 in this state when the endoscope 1 is cleaned, it is possible to retreat most of the elevator 60 from the elevator housing slit 38 and clean the inside of the elevator housing slit 38 and the elevator 60. Thus, cleaning of the distal end portion 7 can be performed easily and promptly.

Moreover, a restricting portion 72 which is one mode of a position restricting portion to restrict the second rotating shaft receiving region 71 from moving to the position of the engaging convex portion 90 of the rotating shaft 82 is protrudingly provided in the proximal end of the coupling portion 64 of the elevator 60, such that the elevator 60 and the rotating shaft 82 are in a state in which they are always coupled with each other when the endoscope 1 is normally used for operation. The restricting portion 72 is described later.

Here, the distal end of the engaging convex portion 90 of the rotating shaft 82 and the side wall portion 34 are closely disposed to each other as mentioned above, and, since the movement in the axis direction of the rotating shaft 82 of the coupling portion 64 is restricted, the rotating shaft receiving portion 66 is prevented from being detached from the engaging convex portion 90 of the rotating shaft 82 and the elevator 60 is prevented from being detached from the elevator housing slit 38.

The function of the above-mentioned distal end portion 7 is described.

FIGS. 10A, 11A, 12 and 13 are diagrams illustrating the state of the elevator 60 in the elevator housing slit 38 and are diagrams illustrating the rotating shaft 82 (the engaging convex portion 90), the elevator 60 and the side wall portion 36, and so on, when the side wall portion 36 is seen from a surface which is vertical to the axis of the rotating shaft 82 and which passes through the position of the engaging convex portion 90 of the rotating shaft 82. FIGS. 10B and 11B are diagrams illustrating the state of the erecting lever 84 in the erecting lever housing chamber 40 of the side wall portion 34.

Figure 10A:
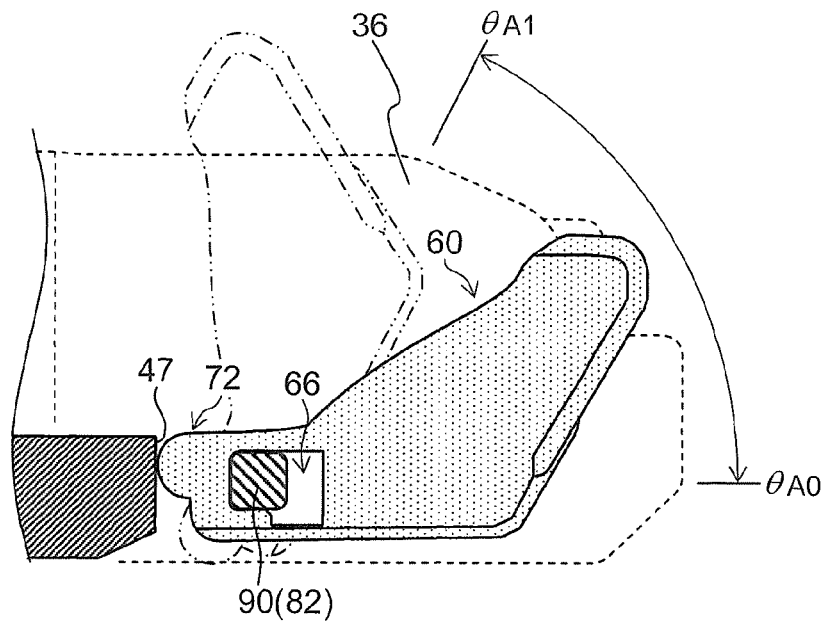
FIGS. 10A and 10B are explanatory drawings used to describe a function of the distal end portion.
Figure 10B:
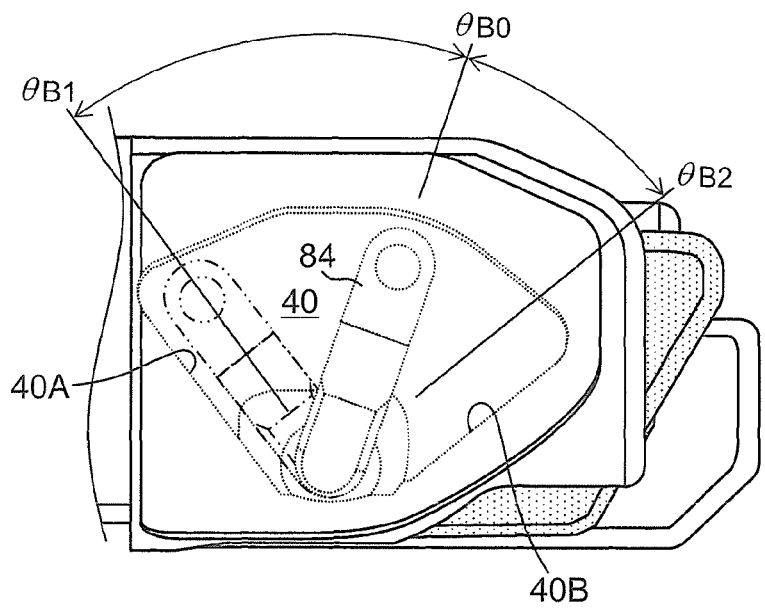

FIGS. 10A and 10B illustrate a state when the cap 26 is attached to the distal end portion 7 and the endoscope 1 is used for operation. When the cap 26 is attached to the distal end portion 7, in the elevator 60, a rotation range toward the reclining side is limited by abutting on the cap 26 so as to limit a rotation range in which at least the elevator 60 is not exposed from the opening portion 38c on the lower surface side of the elevator housing slit 38. Moreover, a rotation range toward the erecting side is limited by abutting on the distal end portion body 30, and so on.

By this means, for example, the rotation range of the elevator 60 which can be operated by the erecting operation lever 12 of the operation portion 3 (a rotation angle range around the rotating shaft 82) is limited within the rotation range from θA0 to θA1 as illustrated in FIG. 10A.

Moreover, assuming that the rotation range of the erecting lever 84 at this time (a rotation angle range around the rotating shaft 82) is limited within a rotation range from θB0 to θB1 as illustrated in FIG. 10B, θB0 is on the erecting side with respect to (from) a position in which the erecting lever 84 abuts on a side wall 40B on the reclining side of the erecting lever housing chamber 40. Here, θB1 substantially matches a position when the erecting lever 84 abuts on the side wall portion 40A on the erecting side of the erecting lever housing chamber 40, it is not necessarily limited to this.

Figure 11A:
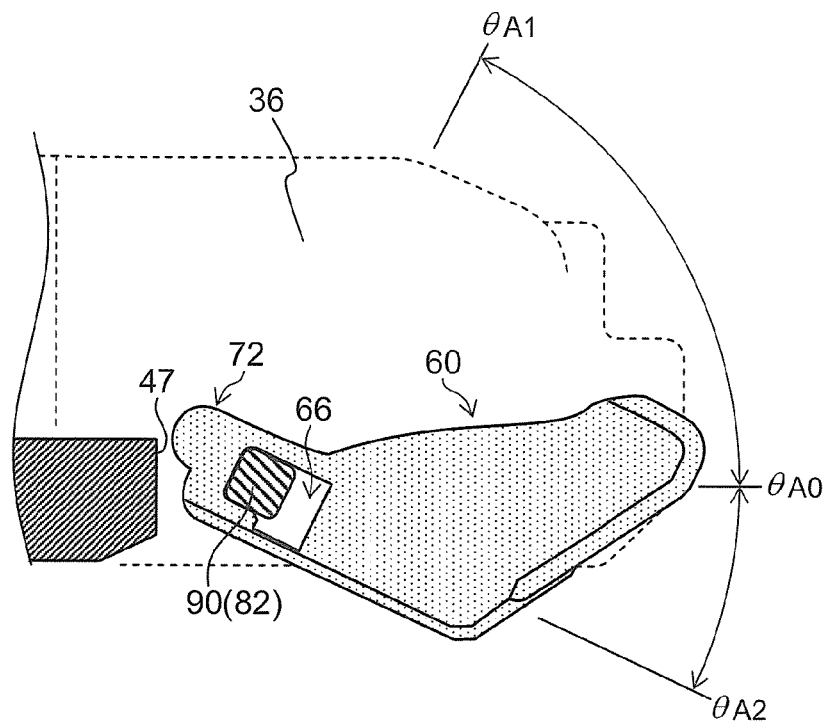
FIGS. 11A and 11B are explanatory drawings used to describe the function of the distal end portion.
Figure 11B:
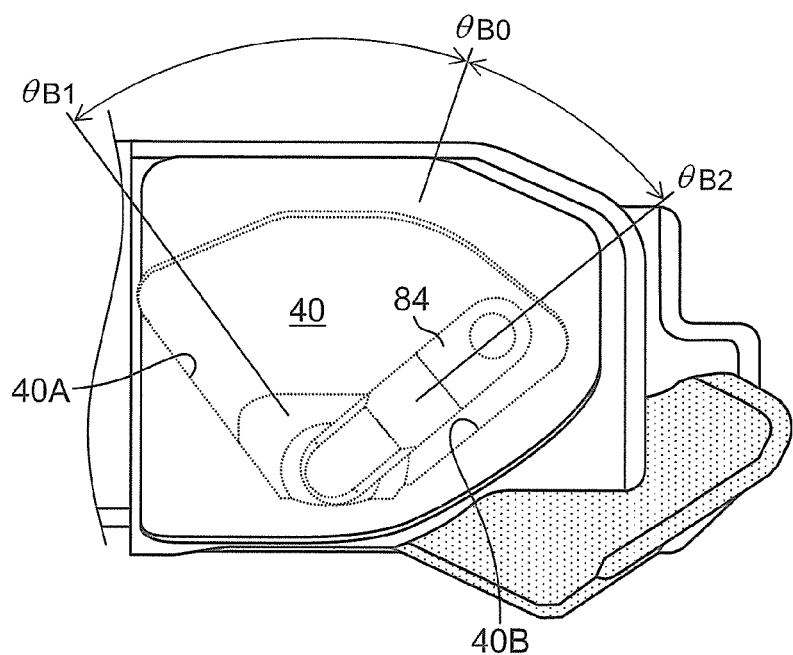

Meanwhile, when the distal end portion 7, and so on, is cleaned after the endoscope 1 is used for operation, the cap 26 is detached from the distal end portion 7. By this means, the rotation restriction on the reclining side of the elevator 60 by the cap 26 is released. Further, it becomes possible to rotate the erecting lever 84 to reach the position of θB2 on the reclining side from θB0 as illustrated in FIG. 11B, and the rotation range of the elevator 60 which can be operated by the erecting operation lever 12 of the operation portion 3 expands to θA2 as illustrated in FIG. 11A.

Figure 12:
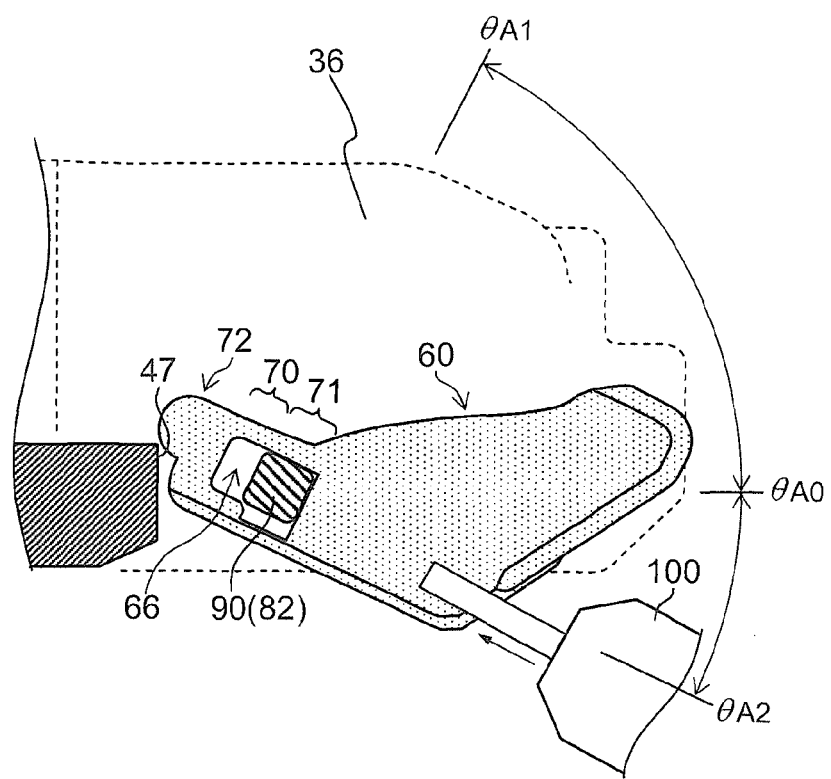
FIG. 12 is an explanatory drawing used to describe the function of the distal end portion.

Further, in a state in which the elevator 60 is set to the reclining side with respect to (from) at least θA0, more preferably, in a state in which the elevator 60 is exposed from the opening portion 38c on the lower surface side of the elevator housing slit 38 to the outside, if the elevator 60 is pushed toward the proximal end side using a jig 100 or the like as illustrated in FIG. 12, the elevator enters a state in which the second rotating shaft receiving region 71 is loosely fitted to the engaging convex portion 90 in the rotating shaft receiving portion 66 of the elevator 60. That is, the coupling between the elevator 60 and the rotating shaft 82 is released.

Here, the jig 100 may be the one with a rod member fitted to a hole formed in the elevator 60 or the one to sandwich the elevator 60, and so on, and is not limited to a specific one. Moreover, the jig 100 need not be used.

Figure 13:
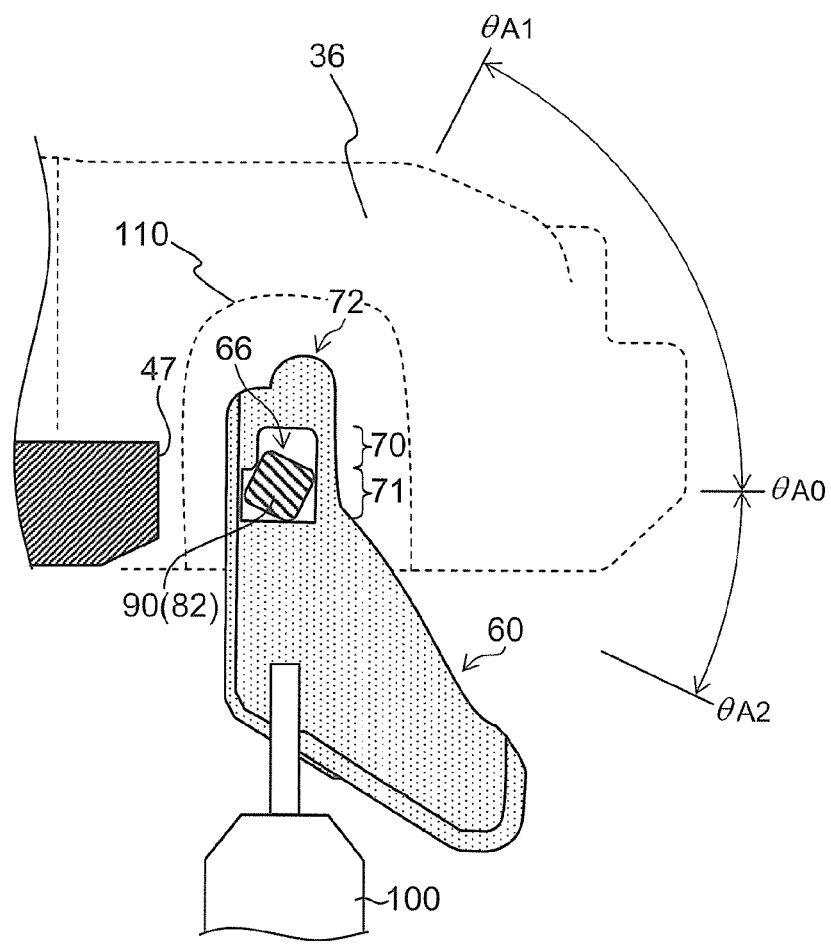
FIG. 13 is an explanatory drawing used to describe the function of the distal end portion.

By this means, it is possible to further rotate the elevator 60 without the rotation of the erecting lever 84 and the rotating shaft 82, and retreat most of the elevator 60 from the elevator housing slit 38 as illustrated in FIG. 13 so as to expose the elevator 60 to the outside. Therefore, since the gap between the elevator 60 and the wall surface of the elevator housing slit 38 is small and the exposed portion of the wall surface of the elevator housing slit 38 increases, it is possible to clean the elevator 60 and the inside of the elevator housing slit 38 easily and promptly.

Here, like FIGS. 10A, 11B and 12, when the position of the elevator 60 in the rotation direction is a position on the erecting side with respect (from) at least θA0, more preferably, a position on the erecting side with respect to (from) a position in which the elevator 60 is exposed from the opening portion 38c on the lower surface side of the elevator housing slit 38 to the outside, the elevator 60 is treated as being located in the first position in the rotation direction, and the restricting portion 72 protrusively provided to the proximal end of the elevator 60 abuts on the wall surface or the like (for example, the lower surface portion of the opening portion 14a of the treatment tool insertion channel 14) of the distal end portion body 30.

By this means, the elevator 60 is restricted to a position in which the first rotating shaft receiving region 70 of the rotating shaft receiving portion 66 of the elevator 60 is engaged with the engaging convex portion 90 of the rotating shaft 82. Therefore, when the endoscope 1 is normally used for operation, the coupling between the elevator 60 and the rotating shaft 82 is not released. Here, the first position can be a position in which the whole of the elevator 60 is housed inside the elevator housing slit 38.

Meanwhile, when the position of the elevator 60 in the rotation direction is a position on the reclining side from at least θA0, more preferably, a position on the reclining side with respect to (from) a position in which the elevator 60 is exposed from the opening portion 38c on the lower surface side of the elevator housing slit 38 to the outside, the elevator 60 is treated as being in the second position in the rotation direction, and the restricting portion 72 allows the elevator 60 to move to a position in which the second rotating shaft receiving region 71 of the rotating shaft receiving portion 66 of the elevator 60 is loosely fitted to the engaging convex portion 90 of the rotating shaft 82.

Here, the second position can be a position in which at least a part of the elevator 60 is exposed to the outside of the elevator housing slit 38, more preferably, a position in which at least a part of the elevator 60 is exposed from the opening portion 38c on the lower surface side of the elevator housing slit 38 to the outside. In addition, the second position can be a position in which at least a part of the elevator 60 is exposed from the opening portion 38a on the upper surface side of the elevator housing slit 38 to the outside.

Figure 14:
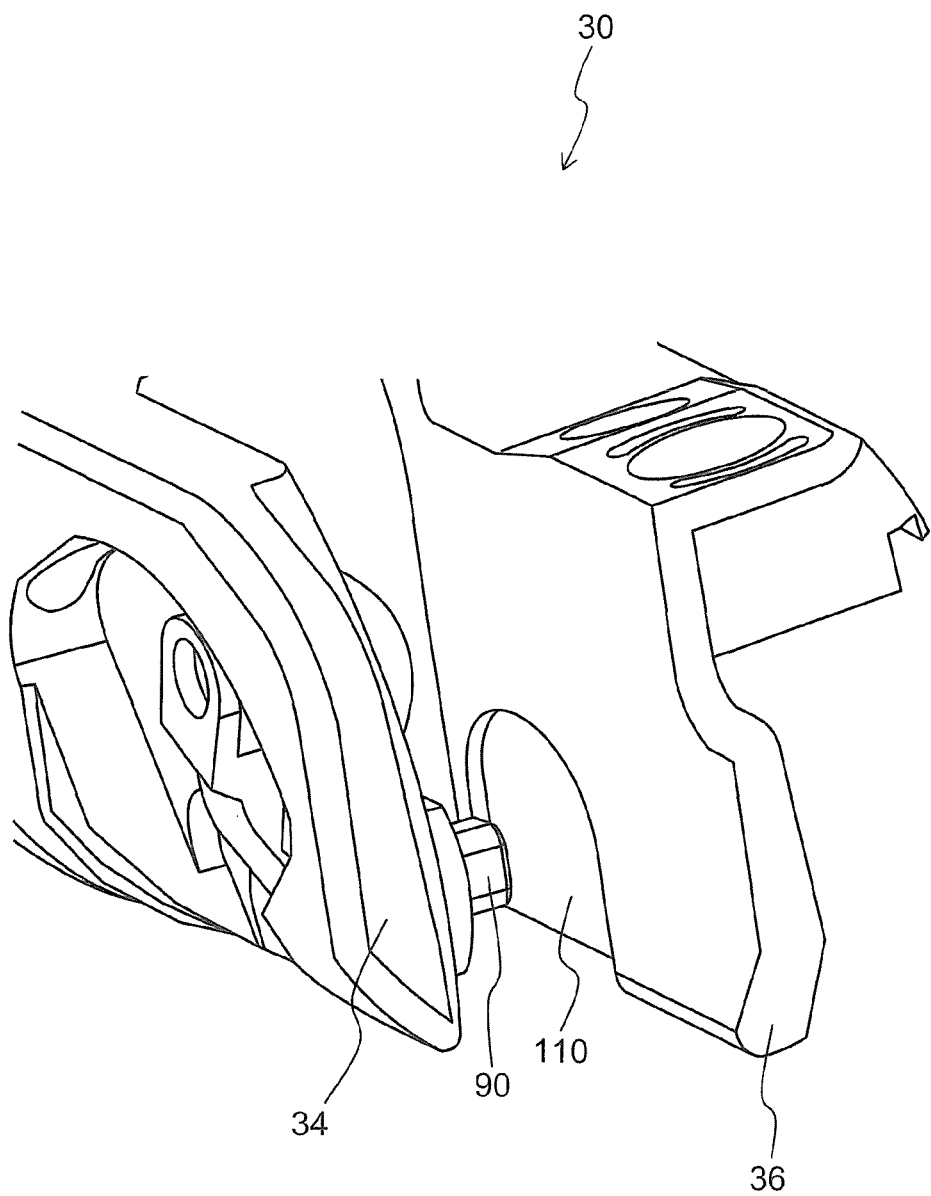
FIG. 14 is an explanatory drawing used to describe the function of the distal end portion.

As above, in the above-mentioned embodiment, for example, as illustrated in FIG. 14, a concave portion 110 which communicates with the lower end from a region opposed to the rotating shaft 82 may be formed in the side wall portion 36. When the range of that concave portion 110 is shown by the broken line in FIG. 13, after the coupling between the elevator 60 and the rotating shaft 82 is released as mentioned above, the elevator 60 is rotated to reach an angle at which it overlaps a range in which the concave portion 110 is formed, like the elevator 60 in FIG. 13. Further, by sliding the elevator 60 in the shaft direction of the rotating shaft 82, it is possible to completely detach the elevator 60 from the elevator housing slit 38 through the concave portion 110 and perform cleaning, and so on.

Moreover, in a similar way to the above-mentioned embodiment, when the elevator 60 is in a rotation range on the erecting side with respect to (from) a predetermined angle. For example, the endoscope can be configured so that the coupling between the elevator 60 and the rotating shaft 82 can be released when the elevator 60 is in a rotation range in which the elevator 60 is exposed from the opening portion 38a on the upper surface side of the elevator housing slit 38 to the outside.

What is claimed is:

1. An endoscope comprising:
    an insertion portion which includes a distal end and a proximal end;
    an operation portion which is provided on a proximal end side of the insertion portion and includes an operating member and;
    a distal end portion body which is provided on a distal end side of the insertion portion, and has a front surface being a surface in a longitudinal direction of the insertion portion, an upper surface being a surface in a direction in which a treatment tool is led out with respect to the longitudinal direction and a lower surface being a surface on a side opposite to the upper surface with respect to the longitudinal direction;
    an elevator which is rotatably provided in the distal end portion body;
    a rotating shaft provided with an axis and configured to rotate the elevator around the axis;

a rotating shaft receiving portion provided in the elevator, the rotating shaft receiving portion including a first rotating shaft receiving region, wherein the rotating shaft does not relatively rotate with respect to the first rotating shaft receiving region by engaging the rotating shaft with the first rotating shaft receiving region, and a second rotating shaft receiving region which is loosely fitted to the rotating shaft in a relatively rotatable manner, wherein the first rotating shaft receiving region and the second rotating shaft receiving region are arranged along a direction perpendicular to a longitudinal axis of the rotating shaft, and the rotating shaft is slidable between the first rotating shaft receiving region and the second rotating shaft receiving region along the direction perpendicular to the longitudinal axis of the rotating shaft;

an elevator erecting mechanism configured to rotate the rotating shaft;

an operating wire which includes a proximal-end-side coupling portion coupled with the operating member and a distal-end-side coupling portion coupled with the elevator erecting mechanism, the operating wire being configured to rotate the rotating shaft to recline or erect the elevator by being pushed or pulled by an operation of the operating member;

an elevator housing slit which is provided in the distal end portion body and forms a space portion to house the elevator, the elevator housing slit including an opening on a side of the upper surface, on a side of the lower surface and on a side of the front surface; and a cap which is detachably provided in the distal end portion body, the cap including an opening window which opens a part of the opening on the side of the upper surface and a partition wall portion which closes a part of the opening on the side of the lower surface in a state in which the cap is attached to the distal end portion body, wherein:

the elevator includes a position restricting portion which is configured to restrict a position of a rotating shaft receiving region of the rotating shaft receiving portion with respect to the rotating shaft; and when the elevator is located in a first position in a rotation direction, the position restricting portion restricts the position of the rotating shaft receiving region of the rotating shaft receiving portion with respect to the rotating shaft to the first rotating shaft receiving region, and, when the elevator is located in a second position in the rotation direction, the position restricting portion allows the position of the rotating shaft receiving region of the rotating shaft receiving portion with respect to the rotating shaft to move from the first rotating shaft receiving region to the second rotating shaft receiving region.

2. The endoscope according to claim 1, wherein the first position is a position in which a whole of the elevator is housed inside the elevator housing slit.

3. The endoscope according to claim 1, wherein the second position is a position in which at least a part of the elevator is exposed to outside of the elevator housing slit.

4. The endoscope according to claim 3, wherein the second position is a position in which at least a part of the elevator is exposed from the part of the opening on the side of the lower surface to outside.

5. The endoscope according to claim 3, wherein the second position is a position in which at least a part of the elevator is exposed from the part of the opening on the side of the upper surface to outside.

6. The endoscope according to claim 1, wherein the rotating shaft is configured in a cantilever shape in which one end of the rotating shaft is a fixed end fixed to the elevator erecting mechanism and another end is a free end.

7. The endoscope according to claim 1, wherein:
the elevator erecting mechanism includes an elevator erecting lever coupled with the rotating shaft;
the distal-end-side coupling portion of the operating wire is coupled with the elevator erecting lever; and
when the operating wire is pushed or pulled by operation of the operating member, the operating wire rotates the rotating shaft through the elevator erecting lever to recline or erect the elevator.

8. The endoscope according to claim 1, wherein an area of a cross section of the first rotating shaft receiving region vertical to a direction of the axis is smaller than a cross section of the second rotating shaft receiving region vertical to the direction of the axis.

9. The endoscope according to claim 1, wherein:
a cross section of the rotating shaft vertical to a direction of the axis has a non-circular shape,
the first rotating shaft receiving region includes an engagement hole which agrees with a shape and a size of the cross section of the rotating shaft, and
the second rotating shaft receiving region includes a larger hole than the cross section of the rotating shaft.

10. The endoscope according to claim 1, wherein the position restricting portion includes a protruded portion that abuts on the distal end portion body to restrict movement of the rotating shaft from the first rotating shaft receiving region to the second rotating shaft receiving region when the elevator is located in the first position in the rotation direction.

* * * * *